United States Patent [19]

Curutchet

[11] 4,140,124
[45] Feb. 20, 1979

[54] HANDLES FOR SURGICAL INSTRUMENTS

[76] Inventor: Pedro D. Curutchet, Sarmiento 156, 7635 Loberia, Argentina

[21] Appl. No.: 813,783

[22] Filed: Jul. 7, 1977

[30] Foreign Application Priority Data

Jul. 14, 1976 [AR] Argentina .............................. 263955

[51] Int. Cl.² ........................................... A61B 17/32
[52] U.S. Cl. .................................. 128/318; 128/305; 30/194; 30/232; 81/428 R; 81/177 C; 81/415
[58] Field of Search ................... 128/318, 321, 305 R, 128/322, 346, 314, 315, 317, 303 R, 320, 325; 30/232, 244, 249, 250, 252, 298, 314, 340, 341, 194; 32/46; 81/428 R, 415, 177 C

[56] References Cited

U.S. PATENT DOCUMENTS

| 440,436 | 11/1890 | Pearsall | 30/341 |
|---|---|---|---|
| 1,438,374 | 12/1922 | Guerrero | 30/341 X |
| 2,669,991 | 2/1954 | Curutchet | 30/341 X |
| 2,669,993 | 2/1954 | Curutchet | 81/428 R X |
| 3,407,816 | 10/1968 | Curutchet | 128/318 |

*Primary Examiner*—Henry J. Reola
*Attorney, Agent, or Firm*—Ladas, Parry, Von Gehr, Goldsmith & Deschamps

[57] ABSTRACT

A surgical instrument comprises first and second elongate members which are pivoted together intermediate their ends in crossing relationship, so as to define a major plane of the instrument extending substantially perpendicular to the axis of pivotal movement of the members and in which the members move during relative pivotal movement thereof. Each member has at a forward end an operating portion which cooperates with the operating portion of the other member when the two operating portions are brought together by relative pivotal movement of the two members, and each member has at its opposite, rearward end an actuating portion which can be urged towards the actuating portion of the other member for bringing the operating portions into cooperating disposition. The actuating portion of the first member comprises a generally triangular member for fitting in the palm of the surgeon's hand and having a first side forming a continuation of the first member, a second side connected to the first side at the forward end thereof and extending rearwardly and in a direction away from the actuating portion of the first member, and a third side connecting the rearward ends of the first and second sides. The triangular member defines a plane which is inclined at substantially 50° to 60° to the major plane, and the third side of the triangular member is provided with holding means for engaging at least one of the surgeon's fingers thereby to hold the second member against movement. The actuating portion of the second member comprises a housing for receiving the distal end of the surgeon's thumb when the triangular member is fitted in the surgeon's palm to urge the second member towards or away from the first member.

7 Claims, 5 Drawing Figures

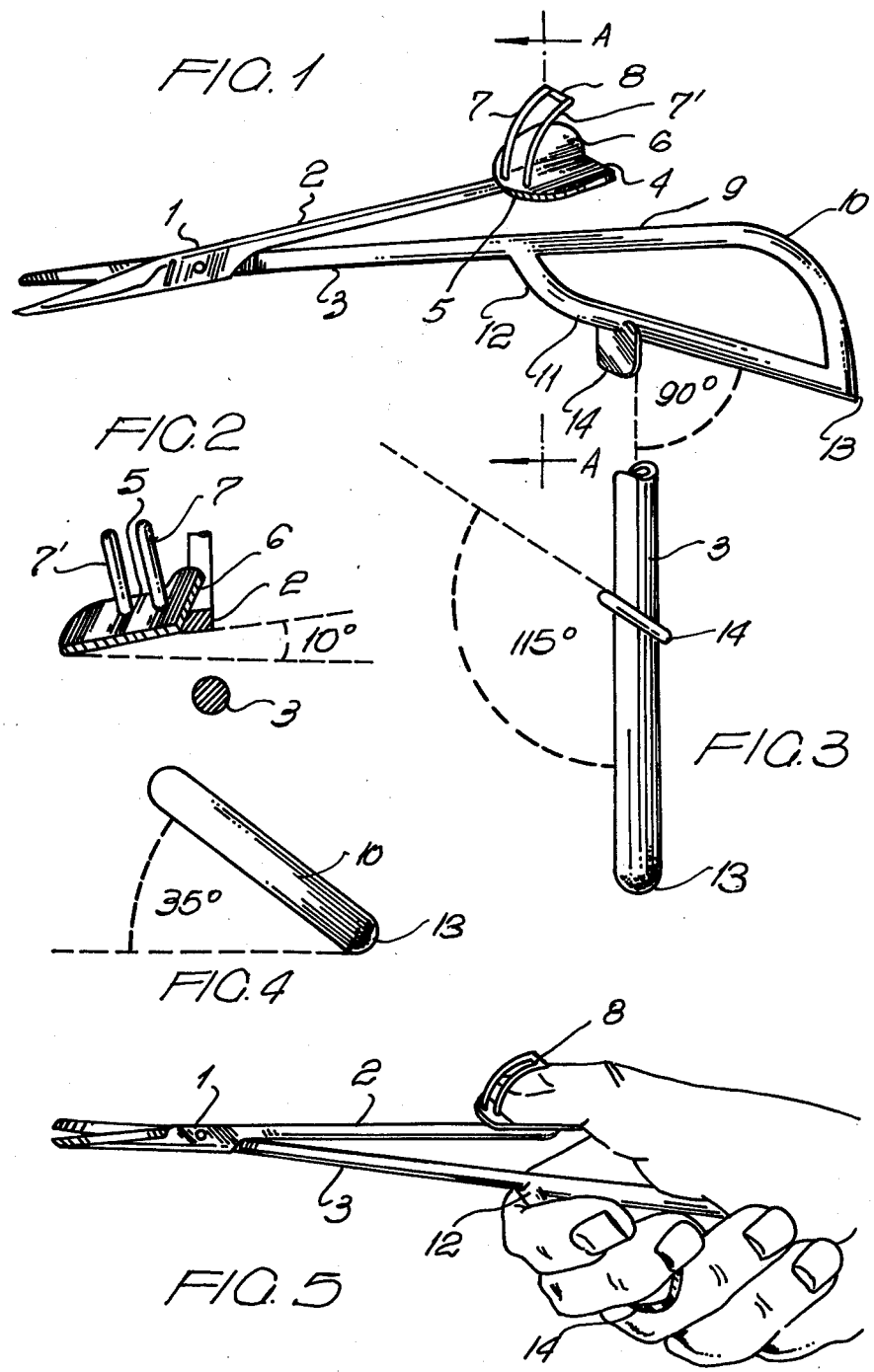

HANDLES FOR SURGICAL INSTRUMENTS

This invention relates to surgical instruments, and in particular to surgical instruments such as scissors which comprise two elongate members which are pivoted together intermediate their ends in crossing relationship.

Scissors which are at present used by surgeons may be termed crucimanual ring instruments, since they extend across the longitudinal axis of the hand and the thumb and the index and middle fingers are inserted in rings to grip and actuate the instrument. Use of such instruments can be traced to the scissors of the barber-surgeons of the XV and XVI centuries. Crucimanual scissors are satisfactory for a barber because the barber cuts flat at the surface. The surgeon, on the contrary, cuts in the depth-wise direction along the axis of the hand and therefore, a crucimanual instrument is not well-suited to use in surgery.

For example, the index finger does not in fact actuate the scissors but is introduced into the ring of the middle finger as a live splint. All the fingers have to be used in order to prevent sideways movement of the scissors. The index finger has to push against the ring in which it is introduced in order to increase the cutting depth. All these disadvantages arise from the fact that the scissors are a crucimanual ring instrument.

According to the present invention there is provided a surgical instrument comprising first and second elongate members which are pivoted together intermediate their ends in crossing relationship, so as to define a major plane of the instrument extending substantially perpendicular to the axis of pivotal movement of the members and in which the members move during relative pivotal movement thereof, each member having at a forward end an operating portion which cooperates with the operating portion of the other member when the two operating portions are brought together by relative pivotal movement of the two members, and each member having at its opposite, rearward end an actuating portion which can be urged towards the actuating portion of the other member for bringing the operating portions into cooperating disposition, the actuating portion of the first member comprising a generally triangular member for fitting in the palm of the surgeon's hand and having a first side forming a continuation of the second member, a second side connected to the first side at the forward end thereof and extending rearwardly and in a direction away from the actuating portion of the first member, and a third side connecting the rearward ends of the first and second sides, the triangular member defining a plane which is inclined at substantially 50° to 60° to said major plane, and the second side of the triangular member being provided with holding means for engaging at least one of the surgeon's fingers thereby to hold said second member against movement, said holding means comprising a sheet-form member secured to the triangular member at said second side thereof, there being an angle of substantially 100° to 120°, measured in a plane perpendicular to the plane of said triangular member and including said second side, included between said second side and said sheet-form member, and an angle of substantially 80° to 100°, measured in the plane of said triangular member, included between the sheet-form member and the region of said second side to the rear of said sheet-form member, and the actuating portion of the second member comprising a housing for receiving the distal end of the surgeon's thumb when said triangular member is fitted in the surgeon's palm, said housing including a base plate for enabling the thumb to apply force to urge the actuating portion of the second member towards the actuating portion of the first member and restraining means for preventing forward movement of the thumb along the second member and for preventing movement of the thumb away from the base plate for enabling the thumb to exert force to urge the actuating portion of the second member away from the actuating portion of the first member, said restraining means comprising first and second mutually parallel wire-like members extending from a forward region of said base plate in a direction away from the actuating portion of the first member and towards the rear, and a third wire-like member which joins the rear ends of the first and second wires.

When an instrument in accordance with the invention is in use, the triangular member is fitted in the palm of the user's hand and the thumb actuates the second elongate member. The instrument extends along the axis of the user's hand and may therefore be termed an aximanual instrument. The present invention is applicable to scissors and to other pivoted instruments, such as needle holders.

In order to make the invention more easily understood and carried out, a preferred embodiment is illustrated by way of example in the enclosed drawings;

FIG. 1 is a view in perspective of a pair of surgical scissors;

FIG. 2 is a sectional view along line A—A of FIG. 1;

FIG. 3 is a top view of the lower portion of the handle;

FIG. 4 is an elevation of part of the handle taken from the rear portion thereof; and FIG. 5 is a view in perspective showing the use of the pair of surgical scissors.

The illustrated surgical scissors comprise an upper branch 2 and a lower branch 3 pivotally connected in conventional manner at 1. The lower branch 3 may be called the master branch since it remains stationary in respect of the surgeon's hand owing to its support in the palm of the hand, and it constitutes a constant and sure reference for the incision.

The upper branch 2 is provided at its internal rear end with a housing member for the thumb of the surgeon, as it can be seen in FIG. 5.

Said housing member for the thumb is constituted by a plate that has a rear edge 4 and a front zone 5, and it has, extending from its external side edge, a substantially flat projection 6 which forms with the plate a dihedral obtuse angle.

From the front zone 5 project upwardly two wire-like members 7,7' which obliquely extend backwards, their ends being connected by a transverse wire-like member 8 which forms substantially a right angle with the members 7,7' and constituting, as shown in FIG. 5, an upper support for the surgeon's thumb that is thus confined in the dihedron formed by the plate and its projection 6 and the members 7,7' and 8, thus being able to displace the branch 2 upwardly or downwardly depending on the movement of the thumb.

The longitudinal plane of the housing member forms with the longitudinal axis of the branch 2 an angle open to the front having a value of from 0 to 50, while the plane of the plate forms with the major plane of the instrument, formed by the branches 2 and 3, an angle of from 80° to 85° counted clockwise with respect to the major plane, the middle sagittal plane of the housing being parallel with the major plane of the instrument.

The lower branch 3 is in turn provided with a member consisting of tube forming a frame having the shape of an arch with a front portion 9 which immediately follows the lower branch and has a straight axis and a curved rear portion 10, the frame being closed by a straight section 11 connected to the lower branch by its front curved end 12 and forming by its rear end meeting the rear portion 10 of the portion 9 in a vertex 13.

The curved rear portion 10 is anatomically adapted to the hollow of the hand while the curved front end 12 can be held by the surgeon's index finger. The middle plane of the frame forms an angle of from 50° to 60° that opens to the outside of the instrument with the major plane of the instrument, as shown in FIG. 4.

Intermediate the ends of the straight section 11 is arranged a smmall plate-like member 14 of substantially rectangular outline, the plane of which forms with the axis of the section 11 an angle of from 100 to 120°, the member keeping in addition an inclination of from 80° to 100° in respect of said section, see FIGS. 1 and 3, respectively, that show said angles, the second of which is open to the rear and to the outside as indicated in FIG. 3.

The small plate-like member 14 acts as a a stabilizer, since once the middle and ring fingers of the surgeon are placed at each side, they secure the instrument and prevent any possible skidding.

As clearly shown in FIG. 2, the position of the housing member at the side of the upper branch 2 enables the thumb and index fingers of the user to be drawn near in a very favorable manner for actuating the instrument. Besides, when the nail of the thumb lifts the members 7, 7' and 8 and therewith the branch 2, the middle finger engages the stabilizer member 14 and acts to retain the convexity of the curved rear portion 10 fitted in the hollow of the hand as shown in FIG. 5. Thus, it may be said that the frame fits in the hollow of the hand but is held by the middle finger.

The manner of operation of the illustrated scissors is to be contrasted with the operation of pivoted instruments (scissors, needle-holders, etc.) of conventional type in which the two blades or jaws move simultaneously like the legs of a cot. This detracts from the precision of the directional movement of the distal ends of the branches. It is necessary that one of the distal ends remain stationary in order to direct the cutting or holding movement, as is the case with the beak of birds, and in the fishes, mammals and humans where the upper jaw is secured to the skull. In the case of the illustrated scissors the palm of the hand supports the instruments and holds stationary the lower branch so that the upper blade can be aimed without any oscillation and accomplish its objective with the utmost precision and safety.

The stationary blade of the scissors (or the stationary jaw of a needle-holder) can be given a metallic color in order to differentiate it from the movable blade (or jaw). And it is preferred in the case of scissors that the edge of the stationary colored blade be, situated on the internal side in order to be clearly visible. In the case of ring scissors with their blades moving simultaneously there is no guidance provided by a stationary blade, and therefore there would be no purpose in coloring them.

The stationary blade being thus in the internal side, the thick rear edge, opposite the stationary edge, does not hinder the sight of the blade that is stationary and guides the cutting operation. The respective handles of the scissors are also colored.

Both the color of the upper blade and the positioning thereof in the internal side are determined by the support given to the handle by the hollow of the hand: without this firm support, the color and internal position of the blade would be to no purpose.

The handle of the scissors colored in gold, for instance, prevents any confusion with the branches and also mistaking the scissors for another aximanual instrument.

As it can be clearly understood by those skilled in the art, there can be introduced variations of detail that do not modify the essence of the invention that has been described and illustrated by way of example having reference to one of its possible embodiments.

What is claimed is:

1. A surgical instrument comprising first and second elongate members which are pivoted together intermediate their ends in crossing relationship, so as to define a major plane of the instrument extending substantially perpendicular to the axis of pivotal movement of the members and in which the members move during relative pivotal movement thereof, each member having at a forward end an operating portion which cooperates with the operating portion of the other member when the two operating portions are brought together by relative pivotal movement of the two members, and each member having at its opposite, rearward end an actuating portion which can be urged towards the actuating portion of the other member for bringing the operating portions into cooperating disposition, the actuating portion of the first member comprising a generally triangular member for fitting in the palm of the surgeon's hand and having a first side forming a continuation of the second member, a second side connected to the first side at the forward end thereof and extending rearwardly and in a direction away from the first side of the actuating portion of the first member, and a third side connecting the rearward ends of the first and second sides, the triangular member defining a plane which is inclined at substantially 50° to 60° counted with respect to said major plane in a clockwise direction, and the second side of the triangular member being provided with holding means for engaging at least one of the surgeon's fingers thereby to hold said second member against movement, said holding means comprising a sheet-form member secured to the triangular member at said second side thereof, there being an angle of substantially 100° to 120° counted, with respect to the plane of the triangular member in a clockwise direction, and measured in a plane perpendicular to the plane of said triangular member that intersects said second side, and between said perpendicular plane and said sheet-form member, there being an angle of substantially 80° to 100° counted with respect to said perpendicular plane in a clockwise direction, and the actuating portion of the second member comprising a housing for receiving the distal end of the surgeon's thumb when said triangular member is fitted in the surgeon's palm, said housing including a base plate for enabling the thumb to apply force to urge the actuating portion of the second member towards the actuating portion of the first member and restraining means for preventing forward movement of the thumb along the second member and for preventing movement of the thumb away from the base plate for enabling the thumb to exert force to urge the actuating portion of the second member away from the actuating portion of the first member, said restraining means comprising first and second mutually parallel wire-like members extending from a forward region of said base plate in a direction away from the actuating portion of the first member and towards the rear, and a third wire-like member which joins the rear ends of the first and second wires.

2. An instrument as claimed in claim 1, wherein said base plate extends transversely to said major plane and is secured along one edge to the second member, the plate being provided at said one edge with a projection extending away from the actuating portion of the first member.

3. An instrument as claimed in claim 2, wherein the plate is disposed at an angle from substantially 80° to substantially 85° with respect to said major plane, and said plate and said projection meet in a line extending at an angle from substantially 0° to substantially 5° to said second elongate member.

4. An instrument as claimed in claim 1, wherein the first and second sides of said generally triangular member meet in a curve, the second and third sides of said generally triangular member meet in a vertex and the first and third sides of said generally triangular member meet in a vertex, the third side being curved at its forward end so as to be concave towards the junction between the first and second sides.

5. An instrument as claimed in claim 1, wherein said generally triangular member comprises a frame made up of first, second and third tube portions constituting the first, second and third sides respectively of the generally triangular member.

6. An instrument as claimed in claim 1, being a pair of scissors, wherein said operating portions are blades and the blade of the first elongate member is colored differently from the other blade.

7. An instrument as claimed in claim 1, being a pair of scissors, wherein the generally triangular frame is colored.

* * * * *